US00PP29752P2

(12) United States Plant Patent
Irvine, Jr.

(10) Patent No.: US PP29,752 P2
(45) Date of Patent: Oct. 16, 2018

(54) BASIL PLANT NAMED 'OBSIDIAN'

(50) Latin Name: *Ocimum basilicum*
Varietal Denomination: Obsidian

(71) Applicant: Ball Horticultural Company, West Chicago, IL (US)

(72) Inventor: James Richard Irvine, Jr., North Aurora, IL (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 15/731,422

(22) Filed: Jun. 6, 2017

(51) Int. Cl.
*A01H 5/02* (2018.01)

(52) U.S. Cl.
USPC ..... Plt./258

(58) Field of Classification Search
USPC ..... Plt./258
See application file for complete search history.

*Primary Examiner* — Susan McCormick Ewoldt
*Assistant Examiner* — Karen M Redden
(74) *Attorney, Agent, or Firm* — Audrey Charles

(57) ABSTRACT

A new and distinct cultivar of Basil plant named 'Obsidian', characterized by its deep reddish-purple colored flowers, dark purplish-grey colored foliage, and moderately vigorous, upright growth habit, is disclosed.

1 Drawing Sheet

Latin name of genus and species of plant claimed: *Ocimum basilicum.*

Variety denomination: 'Obsidian'.

BACKGROUND OF THE INVENTION

The present invention relates to a new and distinct cultivar of Basil plant botanically known as *Ocimum basilicum* and hereinafter referred to by the cultivar name 'Obsidian'.

The new cultivar originated in a controlled breeding program in Elburn, Ill. during June 2009. The objective of the breeding program was the development of Basil cultivars with dark purple-colored foliage, and delayed flowering.

The new Basil cultivar was the result of a self-pollination of the proprietary *Ocimum basilicum* breeding selection coded BSL8-1-2-1, not patented, characterized by its dark purple-colored flowers, dark purple-colored foliage, and moderately vigorous, upright growth habit. The new cultivar was discovered and selected as a single flowering plant within the progeny of the above stated self-pollination during June 2011 in a controlled environment in Elburn, Ill.

Asexual reproduction of the new cultivar by terminal stem cuttings since June 2011 in Elburn, Ill. and West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Obsidian' as a new and distinct cultivar of Basil plant:

1. Deep reddish-purple colored flowers;
2. Dark purplish-grey colored foliage; and
3. Moderately vigorous, upright growth habit.

Plants of the new cultivar differ from plants of the parent primarily in having shorter internodes and shorter plant height.

Of the many commercially available Basil cultivars, the most similar in comparison to the new cultivar is 'Red Rubin', not patented. However, in side by side comparisons, plants of the new cultivar differ from plants of 'Red Rubin' in at least the following characteristics:

1. Plants of the new cultivar flower later in the season than plants of 'Red Rubin';
2. Plants of the new cultivar have smaller leaves than plants of 'Red Rubin'; and
3. Plants of the new cultivar have shorter internode length than plants of 'Red Rubin'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Obsidian'. The plants were grown in 4.5-inch pots for 7 weeks in a greenhouse in West Chicago, Ill. Plants were given one pinch at transplant. Plants were grown for an additional five months in 6.5-inch pots to observe flowering.

DETAILED BOTANICAL DESCRIPTION

Figure 1:
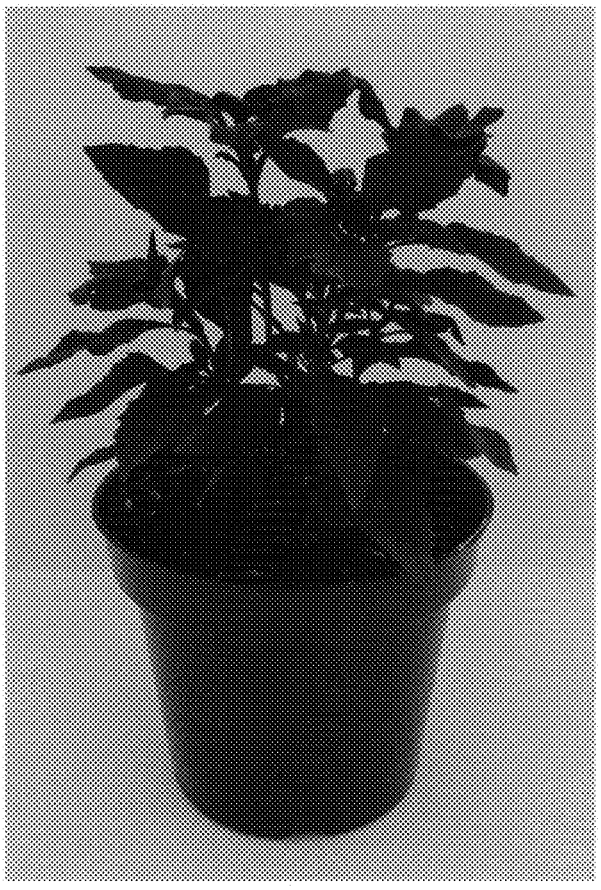
FIG. 1 illustrates a side view of the overall growth and flowering habit of 'Obsidian'.
Figure 2:
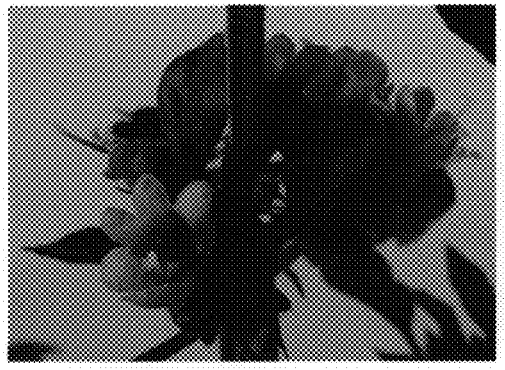
FIG. 2 illustrates a close-up view of an individual leaf of 'Obsidian'.
Figure 3:
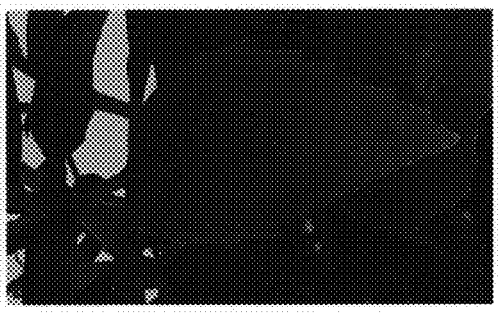
FIG. 3 illustrates a close-up view of flowers of 'Obsidian'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in December 2016 under natural light conditions in West Chicago, Ill.

The following descriptions and measurements describe plants produced from cuttings from stock plants and grown in a glass-covered greenhouse under conditions comparable to those used in commercial practice. The plants were grown in West Chicago, Ill. in 4.5-inch pots for 7 weeks utilizing a soilless growth medium. Plants were given one pinch at transplant. Flower data was collected from plants that were transplanted into 6.5" pots and grown an additional five months. Only one plant was observed to have minimal flowering. Greenhouse temperatures were maintained at approximately 70° F. to 77° F. (21° C. to 25° C.) during the day and approximately 65° F. to 68° F. (18° C. to 20° C.) during the night. Greenhouse light levels of 2,500 footcandles to 6,000 footcandles were maintained during the day. Measurements and numerical values represent averages of typical plants.

Botanical classification: *Ocimum basilicum* cultivar Obsidian.

Parentage:

*Female and male parent*.—Proprietary *Ocimum basilicum* breeding selection coded BSL8-1-2-1, not patented.

Propagation:

*Type cutting*.—Terminal stem.

Propagation:

*Time to initiate roots*.—Approximately 4 to 7 days.

*Time to produce a rooted cutting*.—Approximately 21 to 28 days.

Plant description:

*Root description*.—Fibrous, fine to medium thickness.

*Rooting habit*.—Freely branching.

Plant description:

*Commercial crop time*.—Approximately 6 to 7 weeks from a rooted cutting to finish in a 10 cm pot.

*Growth habit and general appearance*.—Moderately vigorous, upright growth habit.

*Size*.—Height from soil level: Approximately 13.0 cm. Width: Approximately 14.0 cm.

*Branching habit*.—Freely branching, pinching enhances basal branching. Quantity of main branches per plant: Approximately 5.

*Branch*.—Strength: Strong, young stems flexible. Length: Approximately 10.5 cm. Diameter: Approximately 2.0 mm. Length of central internode: Approximately 1.5 cm. Texture: Moderately pubescent. Color of young and mature stems: 146B with a heavy overlay of closest to 187A.

Foliage description:

*General description*.—Quantity of leaves per main branch: Approximately 10. Fragrance: Pungent. Form: Simple. Arrangement: Opposite.

*Leaves*.—Aspect: Primarily perpendicular to stem. Shape: Ovate. Margin: Serrate. Apex: Acute. Base: Attenuate. Venation pattern: Pinnate. Length: Approximately 5.0 cm. Width: Approximately 2.5 cm. Texture of upper and lower surfaces: Glabrous. Color of upper surface of young foliage: Closest to N186A with slightly darker venation. Color of lower surface of young foliage: Closest to 187A with slightly darker venation. Color of upper surface of mature foliage: NN137A with a heavy overlay of closest to N186A and venation of same color as laminae. Green color is less visible under high light conditions. Color of lower surface of mature foliage: NN137B with a heavy overlay of closest to 187A and venation of same color as laminae.

*Petiole*.—Length: Approximately 2.0 mm. Diameter: Approximately 1.0 mm. Texture: Sparsely pubescent. Color: 146B with an overlay of closest to 187A.

Flowering description:

*Flowering habit*.—'Obsidian' might flower very late into growing season, essentially non-flowering.

*Lastingness of individual floret*.—Approximately 4 to 5 days.

Inflorescence description:

*General description*.—Type: Thyrse of opposite two to three flowered cymes.

Flower description:

*Type*.—Single, zygomorphic.

*Bud*.—Rate of opening: Generally takes 2 to 3 days for bud to progress from first color to fully open flower.

*Bud just before opening*.—Shape: Obovoid. Length: Approximately 4.0 mm. Diameter: Approximately 3.0 mm. Texture: Densely pubescent. Color: Calyx of N186A; petals of 145C with pubescence of N82A with N82D.

*Corolla*.—Shape: Bilabiate, upper lip undivided, lower lip having three to four lobes, based fused. Width: Approximately 4.0 mm. Length: Approximately 6.0 mm. Depth: Approximately 1.1 cm. Length of corolla tube: Approximately 5.0 mm. Diameter of corolla tube at opening: Approximately 2.0 mm. Diameter of corolla tube at base: Approximately 1.0 mm.

*Upper lip*.—Shape: Slightly hooded. Margin: Sides entire, apex erose. Apex: Rounded. Length from throat: Approximately 7.0 mm. Width: Approximately 3.0 mm. Texture of inner surface: Glabrous. Texture of outer surface: Moderately pubescent. Color of inner surface when first and fully open: N78D. Color of outer surface when first and fully open: N78C.

*Lower lip*.—Shape of lobes: Oblong, curved downwards. Margin: Entire. Apex of lobes: Rounded. Length from throat of central lobe: Approximately 5.0 mm. Width of central lobe: Approximately 3.0 mm. Length from throat of lateral lobes: Approximately 4.0 mm. Width of lateral lobes: Approximately 2.0 mm. Texture of upper surface: Glabrous. Texture of lower surface: Moderately pubescent. Color of upper surface when first and fully open: N78C. Color of lower surface when first and fully open: N78D.

*Pedicel*.—Strength: Strong, flexible. Length: Approximately 3.0 mm. Diameter: Approximately 1.0 mm. Texture: Densely pubescent. Color: N186A with pubescence of N82A.

*Reproductive organs*.—Androecium: Stamen quantity: 4 per flower. Stamen length: Approximately 1.0 cm. Filament length: Approximately 9.0 mm. Filament color: NN155D with an overlay of N78A. Anther shape: Bilobed, dorsifixed. Anther length: Approximately 1.0 mm. Anther color: 155B. Pollen amount: Abundant. Pollen color: NN155D. Gynoecium: Pistil quantity: 1 per flower, strongly curved. Pistil length: Approximately 1.1 cm. Stigma shape: Bifid. Stigma length: 1.0 mm. Stigma color: NN155D. Style length: Approximately 9.0 mm. Style color: NN155D, with an overlay of N78A that darkens towards ovary. Ovary length: Approximately 1.0 mm. Ovary color: N186A.

Seed and fruit production: Neither seed nor fruit production has been observed.

Disease and pest resistance: Resistance to pathogens and pests common to Basil has not been observed.

What is claimed is:

1. A new and distinct cultivar of Basil plant named 'Obsidian', substantially as herein illustrated and described.

* * * * *